(12) United States Patent
Milligan (10) Patent No.: US 11,453,627 B2
(45) Date of Patent: Sep. 27, 2022

(54) METHOD OF INCREASING ALPHA-OLEFIN CONTENT

(71) Applicant: Liquidpower Specialty Products Inc., Houston, TX (US)

(72) Inventor: Stuart N. Milligan, Ponca City, OK (US)

(73) Assignee: LIQUIDPOWER SPECIALTY PRODUCTS, INC., Houston, TX (US)

(*) Notice: Subject to any disclaimer, the term of this patent is extended or adjusted under 35 U.S.C. 154(b) by 0 days.

(21) Appl. No.: 16/805,259

(22) Filed: Feb. 28, 2020

(65) Prior Publication Data
US 2020/0199044 A1 Jun. 25, 2020

Related U.S. Application Data

(63) Continuation of application No. 15/981,021, filed on May 16, 2018.
(Continued)

(51) Int. Cl.
*C07C 6/04* (2006.01)
*C10G 35/04* (2006.01)
(Continued)

(52) U.S. Cl.
CPC ............ *C07C 6/04* (2013.01); *C08F 10/08* (2013.01); *C08F 10/14* (2013.01); *C10G 35/04* (2013.01);
(Continued)

(58) Field of Classification Search
None
See application file for complete search history.

(56) References Cited

U.S. PATENT DOCUMENTS 3,776,974 A 12/1973 Gautier et al.
3,974,233 A 8/1976 Lawrenson
(Continued)

FOREIGN PATENT DOCUMENTS

CN 101151229 A 3/2008
CN 101180248 A 5/2008
(Continued)

OTHER PUBLICATIONS

Marinescu, S. et al., "Isolation of Pure Disubstituted E Olefins through Mo-Catalyzed Z-Selective Ethenolysis of Stereoisomeric Mixtures". Journal of the American Chemical Society 2011, 133(30), 11512-11514. (Year: 2011).*

(Continued)

*Primary Examiner* — Richard A Huhn
(74) *Attorney, Agent, or Firm* — Patterson + Sheridan, LLP (57) ABSTRACT

Implementations described herein generally relate to methods for purifying alpha-olefins. The alpha-olefins may be used to form drag reducing agents for improving flow of hydrocarbons through conduits, particularly pipelines. In one implementation, a method of increasing alpha-olefin content is provided. The method includes providing an olefin feedstock composition having an alpha-mono-olefin and at least one of a diolefin having an equal number of carbon atoms to the alpha-mono-olefin and/or a triolefin having an equal number of carbon atoms to the alpha-mono-olefin. The method further includes contacting the olefin feedstock composition with ethylene in the presence of a catalyst composition including an olefin metathesis catalyst. The method further includes reacting the olefin feedstock composition and ethylene at metathesis reaction conditions to produce an alpha-olefin product comprising the alpha-
(Continued)

mono-olefin and alpha-olefins having fewer carbon atoms than the alpha-mono-olefin.

28 Claims, 3 Drawing Sheets

Related U.S. Application Data (60) Provisional application No. 62/515,975, filed on Jun. 6, 2017.

(51) Int. Cl.
- *C08F 10/14* (2006.01)
- *C08F 10/08* (2006.01)
- *C07C 4/06* (2006.01)
- *C10G 11/02* (2006.01)
- *C07C 5/27* (2006.01)
- *C07C 5/25* (2006.01)
- *C07C 4/10* (2006.01)

(52) U.S. Cl.
CPC .................. *C07C 4/06* (2013.01); *C07C 4/10* (2013.01); *C07C 5/2587* (2013.01); *C07C 5/2593* (2013.01); *C07C 5/2724* (2013.01); *C09K 2208/28* (2013.01); *C10G 11/02* (2013.01); *C10G 2300/1088* (2013.01); *C10G 2300/30* (2013.01); *C10G 2400/22* (2013.01)

(56) References Cited

U.S. PATENT DOCUMENTS

| | | | |
|---|---|---|---|
| 4,511,753 | A | 4/1985 | Smith et al. |
| 4,697,040 | A | 9/1987 | Williamson et al. |
| 5,210,347 | A | 5/1993 | Chen et al. |
| 5,244,937 | A | 9/1993 | Lee et al. |
| 5,449,732 | A | 9/1995 | Smith et al. |
| 5,504,131 | A | 4/1996 | Smith et al. |
| 5,504,132 | A | 4/1996 | Smith et al. |
| 5,539,044 | A | 7/1996 | Dindi et al. |
| 6,730,750 | B2 | 5/2004 | Eaton et al. |
| 7,812,185 | B2 | 10/2010 | Burdett et al. |
| 7,905,288 | B2 | 3/2011 | Kinkead |
| 7,977,522 | B2 | 7/2011 | Takai et al. |
| 8,569,560 | B2 | 10/2013 | Schrodi et al. |
| 9,175,231 | B2 | 11/2015 | Firth et al. |
| 9,611,193 | B2 | 4/2017 | Choi et al. |
| 10,633,306 | B2 * | 4/2020 | Milligan ................ C10G 69/08 |
| 2002/0016521 | A1 * | 2/2002 | Culver ..................... C07C 2/32 |
| | | | 585/527 |
| 2003/0135080 | A1 | 7/2003 | Botha et al. |
| 2008/0164138 | A1 | 7/2008 | Hill et al. |
| 2008/0188703 | A1 | 8/2008 | Hill et al. |
| 2009/0043140 | A1 | 2/2009 | Yang et al. |
| 2011/0160504 | A1 | 6/2011 | Stephan et al. |
| 2012/0053309 | A1 | 3/2012 | Holtcamp et al. |
| 2013/0035532 | A1 | 2/2013 | Schrodi et al. |
| 2014/0046110 | A1 | 2/2014 | Iselborn et al. |
| 2015/0240186 | A1 | 8/2015 | Cohen et al. |
| 2016/0039737 | A1 * | 2/2016 | Champagne .......... C07C 67/475 |
| | | | 554/126 |

FOREIGN PATENT DOCUMENTS

| | | |
|---|---|---|
| CN | 103080146 A | 5/2013 |
| CN | 104058919 A | 9/2014 |
| CN | 105793217 A | 7/2016 |
| GB | 1471151 A | 4/1977 |
| JP | H7-501088 A | 2/1995 |
| JP | 2016-512854 A | 5/2016 |
| SU | 294314 | 1/1971 |
| WO | 93/06069 A1 | 4/1993 |
| WO | 2006/093058 A1 | 9/2006 |
| WO | 2008/147836 A1 | 12/2008 |
| WO | 2008/153643 A1 | 12/2008 |
| WO | 2012/027139 A2 | 3/2012 |
| WO | 2014/145920 A1 | 9/2014 |

OTHER PUBLICATIONS

Van der Klis, F. et al., "Renewable linear alpha olefins by selective ethenolysis of decarboxylated unsaturated fatty acids", European Journal of Lipid Science and Technology 2012, 114(8), 911-918. (Year: 2012).*

Office Action for Taiwan Application No. 107119043 dated Jan. 9, 2020.

Search Report for Taiwan Application No. 107119043 dated Jan. 9, 2020.

Ohlmann, D. M. et al., Isomerizing Olefin Metathesis as a Strategy To Access Defined Distributions of Unsaturated Compounds from Fatty Acids, J. Am. Chem. Soc. 2012, 134, 13716-13729. (Year: 2012).

International Search Report and Written Opinion for International Application No. PCT/US2018/034092 dated Jan. 4, 2019.

Communication re Hearing Notice for Indian Application No. 201937054285 dated Dec. 30, 2020.

Office Action for Indian Application No. 201937054285 dated Jun. 22, 2020.

Office Action for Russian Application No. 2019143085 dated Mar. 30, 2020.

Search Report for Russian Application No. 2019143085 dated Mar. 30, 2020.

Office Action for Russian Application No. 2019143085 dated Feb. 25, 2021.

Office Action for Japanese Application No. 2019-567735 dated Jul. 13, 2021.

European Search Report in related application EP21167705.9 dated Nov. 15, 2021.

Office Action for Indonesian Application No. P00201911754 dated Jul. 27, 2021.

Canadian Office Action dated Nov. 19, 2021 for Application No. 3,064,562.

Japanese Office Action dated Nov. 16, 2021 for Application No. 2019-567735.

Office Action in related application CN 201880037374.7 dated Feb. 8, 2022.

Office Action in related application IN 202138047054 dated Jul. 12, 2022.

Office Action in related application SA 519410713 dated Jun. 8, 2022.

* cited by examiner

METHOD OF INCREASING ALPHA-OLEFIN CONTENT

CROSS-REFERENCE TO RELATED APPLICATIONS

This application is a continuation of U.S. patent application Ser. No. 15/981,021, filed May 16, 2018, which claims benefit of U.S. Provisional Patent Application Ser. No. 62/515,975, filed Jun. 6, 2017. Each of the aforementioned related patent applications is incorporated herein by reference in its entirety.

BACKGROUND

Field

Implementations described herein generally relate to methods for purifying alpha-olefins, which may be used in, among other things, drag reducing agents for improving flow of hydrocarbons through conduits, particularly pipelines.

Description of the Related Art

The flow of liquid in a conduit, such as a pipeline, typically results in frictional energy losses. Due to this energy loss, the pressure of the liquid in the conduit decreases along the conduit in the direction of the flow. For a conduit of fixed diameter, this pressure drop increases with increasing flow rate. When the flow in the conduit is turbulent (e.g., Reynold's number greater than about 2100), certain ultrahigh molecular weight polymers can be added to the liquid flowing through the conduit to reduce the frictional energy losses and alter the relationship between pressure drop and flow rate. These polymers are sometimes referred to as drag reducing agents ("DRAs"), and they interact with the turbulent flow processes and reduce frictional pressure losses such that the pressure drop for a given flow rate is less, or the flow rate for a given pressure drop is greater. Because DRAs reduce frictional energy losses, increase in the flow capability of pipelines, hoses and other conduits in which liquids flow is possible. DRAs can also decrease the cost of pumping fluids, the cost of equipment used to pump fluids, and provide for the use of a smaller pipe diameter for a given flow capacity. Accordingly, an ongoing need exists to form improved drag reducing materials.

Generally, many commercially available petroleum pipeline DRAs are ultrahigh molecular weight polyalphaolefin polymers that are predominately amorphous, or non-crystalline, are highly linear polymers produced from various alpha-olefin monomers. These alpha-olefin monomers are typically made by oligomerization of ethylene, chemical transformation of select plant oils, or other production methods, and are the feedstock for making DRAs. However, in addition to alpha-olefin monomers, the feedstock from the oligomerization of ethylene or other alpha-olefin production methods may also result in other isomers or the same carbon atom number by-products. The presence of these other isomers may interfere with the polymerization that forms the DRAs. There is a need, therefore, to increase the alpha-olefin content in a feedstock for making, among other things, DRAs. There is also a need for increasing the alpha-olefin content in feedstocks for other olefin chemistries.

SUMMARY

Implementations described herein generally relate to methods for purifying alpha-olefins. The alpha-olefins may be used to form, among other things, drag reducing agents for improving flow of hydrocarbons through conduits, particularly pipelines. In one implementation, a method of increasing alpha-olefin content is provided. The method includes providing an olefin feedstock composition having an alpha-mono-olefin and at least one of a diolefin having an equal number of carbon atoms to the alpha-mono-olefin and/or a triolefin having an equal number of carbon atoms to the alpha-mono-olefin. The method further includes contacting the olefin feedstock composition with ethylene in the presence of a catalyst composition including an olefin metathesis catalyst. The method further includes reacting the olefin feedstock composition and ethylene at metathesis reaction conditions to produce an alpha-olefin product comprising the alpha-mono-olefin and one or more alpha-olefins having fewer carbon atoms than the alpha-mono-olefin. Separation by a method such as distillation results in a fraction that is highly enriched in the alpha-mono-olefin.

In another implementation, a method of increasing alpha-olefin content is provided. The method includes providing an olefin feedstock composition having an alpha-mono-olefin and vinylidene olefins. The method further includes reacting the olefin feedstock composition in the presence of an isomerization catalyst to form an isomerized olefin feedstock having the alpha-mono-olefin and branched internal olefins formed from the vinylidene olefins. The method further includes contacting the isomerized olefin feedstock composition with ethylene in the presence of a catalyst composition having an olefin metathesis catalyst. The method further includes reacting the isomerized olefin feedstock composition and ethylene at metathesis reaction conditions to produce an alpha-olefin product having the alpha-mono-olefin, linear and branched olefins having fewer carbon atoms than the alpha-mono-olefin. Separation by a method such as distillation results in a fraction that is highly enriched in the alpha-mono-olefin.

In yet another implementation, a method of increasing alpha-olefin content is provided. The method includes providing an olefin feedstock composition having 1-decene and at least one of a diolefin having at least 10 carbon atoms and/or a triolefin having at least 10 carbon atoms. The method further includes contacting the olefin feedstock composition with ethylene in the presence of a catalyst composition including an olefin metathesis catalyst. The method further includes reacting the olefin feedstock composition and ethylene at metathesis reaction conditions to produce an alpha-olefin product comprising 1-decene and at least one of terminal olefins having less than 10 carbon atoms and diolefins having less than 10 carbon atoms. Separation by a method such as distillation results in a fraction that is highly enriched in 1-decene.

In yet another implementation, a method of increasing alpha-olefin content is provided. The method includes providing an olefin feedstock composition having 1-decene and vinylidene olefins. The method further includes reacting the olefin feedstock composition in the presence of a zeolite catalyst to form an isomerized olefin feedstock having 1-decene and branched internal olefins formed from the vinylidene olefins. The method further includes contacting the isomerized olefin feedstock composition with ethylene in the presence of a catalyst composition having an olefin metathesis catalyst. The method further includes reacting the isomerized olefin feedstock composition and ethylene at metathesis reaction conditions to produce an alpha-olefin product having 1-decene, linear and branched olefins having less than 10 carbon atoms. Separation by a method such as distillation results in a fraction that is highly enriched in 1-decene.

In yet another implementation, a method of increasing alpha-olefin content is provided. The method includes providing an olefin feedstock composition having a linear internal mono-olefin and optionally at least one of an alpha-olefin having more than 10 carbon atoms, a vinylidene olefin, a diolefin, and/or a triolefin. The method further includes providing a catalyst composition comprising an olefin metathesis catalyst. The method further includes reacting the olefin feedstock composition and ethylene at metathesis reaction conditions in the presence of the catalyst composition to produce an alpha-olefin product comprising an alpha-mono-olefin and one or more alpha-olefins having fewer carbon atoms than the alpha-mono-olefin. Separation by a method such as distillation results in a fraction that is highly enriched in alpha-mono-olefin.

In yet another implementation, a method of increasing alpha-olefin content is provided. The method includes providing an olefin feedstock composition having 3-dodecene and optionally at least one of an alpha-olefin, a vinylidene olefin, a diolefin, and/or a triolefin. The method further includes contacting the olefin feedstock composition with ethylene in the presence of a catalyst composition including an olefin metathesis catalyst. The method further includes reacting the olefin feedstock composition and ethylene at metathesis reaction conditions to produce an alpha-olefin product having 1-decene, linear and branched olefins having less than 10 carbon atoms. Separation by a method such as distillation results in a fraction that is highly enriched in 1-decene.

BRIEF DESCRIPTION OF THE DRAWINGS

So that the manner in which the above-recited features of the present disclosure can be understood in detail, a more particular description of the implementations, briefly summarized above, may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

To facilitate understanding, identical reference numerals have been used, where possible, to designate identical elements that are common to the figures. It is contemplated that elements and features of one implementation may be beneficially incorporated in other implementations without further recitation.

DETAILED DESCRIPTION

The following disclosure describes methods for increasing alpha-olefin content, and more particularly to methods for increasing the purity of alpha-olefin in olefin feedstocks, and methods for forming drag reducing agents incorporating the alpha-olefins. Although discussed in the context of drag reducing agents, the implementations described herein are also applicable to other processes wherein high purity alpha-olefin is desirable. Certain details are set forth in the following description to provide a thorough understanding of various implementations of the disclosure. Other details describing well-known details often associated with isomerization, metathesis and distillation processes are not set forth in the following disclosure to avoid unnecessarily obscuring the description of the various implementations.

Different aspects, implementations and features are defined in detail herein. Each aspect, implementation or feature so defined may be combined with any other aspect(s), implementation(s) or feature(s) (preferred, advantageous or otherwise) unless clearly indicated to the contrary.

As used herein, the singular forms "a," "an," and "the" include plural referents unless the context clearly indicates otherwise.

As used herein, the terms "comprising," "including" and "having" are intended to be inclusive and mean that there may be additional elements other than the listed elements.

As used herein, the term "alpha-olefin" refers to an olefin that has a double bond between the first and second carbon atom. The term "alpha-olefin" includes linear and branched alpha-olefins unless expressly stated otherwise. In the case of branched alpha-olefins, a branch may be at the 2-position (a vinylidene olefin) and/or the 3-position or higher with respect to the olefin double bond. The term "alpha-olefin," by itself, does not indicate the presence or absence of heteroatoms and/or the presence or absence of other carbon-carbon double bonds unless explicitly indicated. The term "hydrocarbon alpha-olefin" or "alpha-olefin hydrocarbon" refers to alpha-olefin compounds containing only hydrogen and carbon. The terms "alpha-olefin" and "terminal olefin" can be used interchangeably.

As used herein, the term "alpha-mono-olefin" refers to a linear hydrocarbon mono-olefin having a double bond between the first and second carbon atom. Examples of alpha-mono-olefins include 1-hexene, 1-heptene, 1-octene, 1-nonene, 1-decene, 1-dodecene, 1-tridecene, 1-tetradecene, 1-hexadecene, 1-octadecene, 1-eicosene, 1-docosene, and the like. The terms "alpha-mono-olefin" and "1-olefin" can be used interchangeably.

As used herein, the term "diolefin" refers to an olefin having an unsaturated hydrocarbon containing two pairs of carbon atoms linked by double bonds.

As used herein, the term "triolefin" refers to an olefin having an unsaturated hydrocarbon containing three pairs of carbon atoms linked by double bonds.

As used herein, the term "olefin metathesis catalyst" includes any catalyst or catalyst system that catalyzes an olefin metathesis reaction.

As used herein, the term "internal olefin(s)" refers to an olefin, which has a double bond at any position other than between the first and second carbon atom. An "internal olefin(s)" can be linear or branched. A "branched internal olefin" may have a branch attached to one of the carbon atoms of the internal double bond and/or may have a branch at any carbon atom other than those participating in the internal olefin double bond. The term "internal olefin(s)" does not indicate the presence or absence of other groups, branches, heteroatoms, or double bonds within the "internal olefin(s)" unless explicitly indicated (e.g., internal mono-olefin). A "linear internal olefin(s)" whenever used in this specification and claims refers to a linear olefin(s) wherein the double bond is not a terminal double bond (e.g., one and only one organyl group attached to each carbon atom of the carbon-carbon double bond). The term "linear internal olefin(s)" does not indicate the presence or absence of other groups, heteroatoms, or double bonds unless explicitly indicated (e.g., linear internal mono-olefin).

As used herein, the term "feedstock olefin(s)" or "olefin feedstock composition" refers to the olefinic compounds, which are originally present in the feedstock composition or the olefin feedstock composition before being contacted with the metathesis catalyst. As used herein, the term "feedstock olefin(s)" or "olefin feedstock composition" does not include any new olefinic compounds produced during the metathesis reaction (via metathesis and/or isomerization reactions), which were not originally present in the "olefin feedstock."

As used herein, the term "alpha-olefin product(s)" refers to organic material(s) produced by a metathesis reaction. The term "alpha-olefin product(s)" refers to material(s) produced by a metathesis reaction having a carbon number equal to or less than the carbon number of the original feedstock olefin(s) having the greatest number of carbon atoms present in a quantity of at least 3 weight percent. The term "alpha-olefin product(s)" includes internal olefins, which may not be alpha-olefins.

As used herein, the terms "isomerization," "isomerizes," or "isomerizing" may refer to the shift of the carbon-carbon double bond to another location in the molecule.

As used herein, the term "vinylidene olefin(s)" whenever used in this specification and claims refers to an alpha-olefin having a branch at the 2-position with respect to the olefin double bond. Vinylidene olefin(s) have the structure $(R_1)(R_2)C=CH_2$, wherein $R_1$ and $R_2$ are the same or, more usually different alkyl groups. Examples of vinylidene olefins include 2-methyl-1-butene, 2-methyl-1-pentene, 2-ethyl-1-octene, 2-ethyl-1-decene, 2-methyl-1-nonene, 2-butyl-1-decene, 2-propyl-1-octene, 2-ethyl-1-dodecene, 2-hexyl-1-decene, 2-ethyl-1-tetradecene, 2-ethyl-1-hexadecene, 2-methyl-1-heptadecene, 2-ethyl-1-octadecene, 2-butyl-1-hexadecene, 2-ethyl-1-eicosene, 2-butyl-1-octadecene, 2-ethyl-1-docosene, and the like.

Alpha-olefins are typically made by oligomerization of ethylene, chemical transformation of select plant oils, or other production methods, and are the feedstock for making drag-reducing polymers. The alpha-olefin (a.k.a. 1-alkene) in the oligomerization or transformation mixture is the most effective in making drag-reducing polymers; all other isomers (e.g., diolefins, triolefins, vinylidene olefins, or internal olefins) present typically interfere with the polymerization to make ultrahigh molecular weight drag-reducing polymers. These other isomers are also typically detrimental to other chemical reactions of alpha-olefins. Thus, although purity of alpha-olefin in feedstocks is frequently 95% or higher, increased alpha-olefin content is desired. One known method claims to improve alpha-olefin feedstocks by isomerizing the 2-ethyl-1-alkenes into branched internal olefins using a zeolite catalyst. However, these resultant branched olefins are no more useful in olefin polymerization to make drag reducing polymers than the precursors, nor are the branched olefins removed.

One implementation of the present disclosure includes a method to purify alpha-olefin feedstock streams by taking the isomerized olefin feedstock resulting from zeolite treatment and performing an olefin metathesis reaction with ethylene followed by distillation to remove lower-boiling fragments. Olefin metathesis with ethylene converts internal olefins and the isomerized products to lower carbon olefins with lower boiling points. Alpha-olefins are essentially unreacted. Although alpha-olefins can undergo metathesis with ethylene, it is a futile reaction, which gives back the same alpha-olefin and ethylene. The by-product olefins can be removed by distillation to provide a feedstock with increased alpha-olefin content. An additional advantage of this method is that it can also be used to produce alpha-olefins of odd carbon numbers by further treatment of lower boiling streams. In addition, other specialty olefins can be isolated using the implementations described herein.

Implementations of the present disclosure relate to methods for producing olefin feedstocks having high purity of alpha-olefins. In one implementation, the alpha-olefin content of in an olefin feedstock composition is increased by contacting the alpha-olefin feedstock containing diolefin and/or triolefin impurities with ethylene in the presence of an olefin metathesis catalyst and distilling out the lower boiling point products. In another implementation, the alpha-olefin content of an olefin feedstock composition is increased by contacting the alpha-olefin feedstock containing vinylidene olefin impurities with an isomerization catalyst, then with ethylene in the presence of an olefin metathesis catalyst and distilling out the lower boiling point products.

Features of the process(es)/methods such as the olefin feedstock, feedstock composition having the olefin feedstock, constraints on the olefins of the olefin feedstock (if any), olefin metathesis catalyst, olefin catalyst composition comprising the olefin metathesis catalyst, constraints of the olefin metathesis catalyst (if any), the isomerized olefin feedstock, the isomerized feedstock composition having the isomerized olefin feedstock, constraints on the olefins of the isomerized olefin feedstock (if any), the zeolite catalyst, the zeolite catalyst composition comprising the zeolite catalyst, constraints of the zeolite catalyst (if any), the alpha-olefin product, constraints for the alpha-olefin product, olefin metathesis reaction conditions, constraints on the olefin metathesis reaction conditions, isomerization reaction conditions, constraints on the isomerization reaction conditions, and other method features and/or steps are independently described herein. These features can be utilized in any combination necessary to describe the process(es)/method(s) to produce the alpha-olefin product having the desired alpha-olefin purity.

In one implementation, the method includes (1) providing an olefin feedstock composition having an alpha-mono-olefin and at least one of a diolefin having an equal number of carbon atoms as the alpha-mono-olefin and/or a triolefin having an equal number of carbon atoms as the alpha-mono-olefin. The method further includes (2) providing a catalyst composition having an olefin metathesis catalyst. The method further includes (3) reacting the olefin feedstock composition and ethylene at metathesis reaction conditions in the presence of the olefin metathesis composition to produce an alpha-olefin product comprising the alpha-mono-olefin and one or more alpha-olefins having fewer carbon atoms than the alpha-mono-olefins. Separation by a method such as distillation results in a fraction that is highly enriched in alpha-mono-olefin. Not to be bound by theory, but it is believed that the alpha-mono-olefin goes through the metathesis reaction unchanged but that the diolefins and triolefins react under the metathesis reaction conditions to form lower molecular weight olefins and diolefins, which can be easily removed by distillation.

Figure 1:
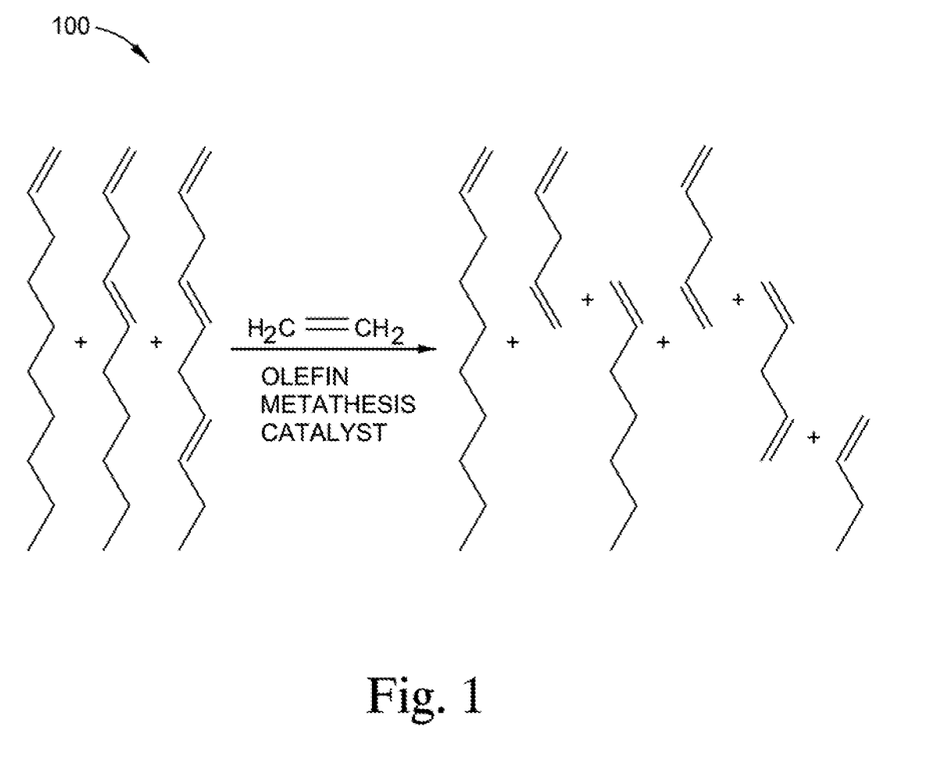
FIG. 1 depicts a first example of a reaction scheme for increasing olefin content according to one or more implementations of the present disclosure.

FIG. 1 depicts a first example of a reaction scheme 100 for increasing olefin content according to one or more implementations of the present disclosure. Referring to FIG. 1, in another implementation, the method includes (1) providing an olefin feedstock composition having 1-decene and at least one of a diolefin having at least 10 carbon atoms and/or a triolefin having at least 10 carbon atoms. The method further includes (2) providing a catalyst composition having an olefin metathesis catalyst. The method further includes (3) reacting the olefin feedstock composition with ethylene at metathesis reaction conditions in the presence of the catalyst composition to produce a product composition having 1-decene and one or more alpha-olefins having less than 10 carbon atoms.

Generally, the olefin feedstock can comprise, or consist essentially of, any olefinic compound. Further features that can be utilized to describe the olefins may include the type of olefins present, the carbon number of the olefins present, the average molecular weight of the olefin(s), and/or the content of a particular type(s) of olefins present (i.e. weight percent or mole percent), among other olefin feedstock features described herein. These features of the olefin feedstock are independently described herein and may be utilized in any combination to describe the olefins of the olefin feedstock.

In one implementation, the olefins of the olefin feedstock can comprise, or alternatively consist of aliphatic olefins, aromatic olefins, or combinations thereof; alternatively, aliphatic olefins; or alternatively aromatic olefins. In some implementations, the olefins of the olefin feedstock (whether aliphatic or aromatic) can comprise, or consist essentially of, linear olefins, branched olefins, or combinations thereof, alternatively, linear olefins; or alternatively, branched olefins. In other implementations, the olefins of the olefin feedstock (whether aliphatic or aromatic, linear or branched, or combinations thereof) can comprise, or consist essentially of acyclic olefins, cyclic olefins, or combinations thereof; alternatively, acyclic olefins, alternatively, cyclic olefins. In some implementations, the olefins of the olefin feedstock (whether aliphatic or aromatic, linear or branched, cyclic or acyclic, or combinations thereof) may comprise, or consist essentially of, hydrocarbon olefins. In one implementation, the olefins of the olefin feedstock (whether aliphatic or aromatic, linear or branched, acyclic or cyclic, hydrocarbon, or combinations thereof) may comprise, or consist essentially of, alpha-olefins. In some implementations, the olefins of the olefin feedstock (whether aliphatic or aromatic, acyclic or cyclic, hydrocarbon, or combinations thereof) may comprise, or consist essentially of, linear alpha-olefins and branched alpha-olefins wherein the branch(es) resides on a carbon atom at the 3-position or higher with respect to the olefin double bond; alternatively, linear alpha-olefins; or alternatively, branched alpha-olefins having the branch(s) at the 3-position or higher with respect to the olefin double bond. In one implementation, the olefins of the olefin feedstock (whether aliphatic or aromatic, linear or branched, acyclic or cyclic, hydrocarbon, or combinations thereof) may comprise, or consist essentially of, hydrocarbon alpha-olefins. In one implementation, the olefins of the olefin feedstock may comprise, or consist essentially of, linear hydrocarbon alpha-olefins; or alternatively, normal alpha-olefins.

In one implementation, the olefins of the olefin feedstock (whether aliphatic or aromatic, linear or branched, cyclic or acyclic, hydrocarbon, alpha-olefin, or any combination thereof) may comprise, or consist essentially of, mono-olefins, diolefins, and/or triolefins. In some implementations, the olefins of the olefin feedstock (whether aliphatic or aromatic, linear or branched, cyclic or acyclic, alpha-olefin, or any combination thereof) may comprise, or consist essentially of, hydrocarbon mono-olefins, diolefins, and/or triolefins. In some implementations, the olefins of the olefin feedstock (whether aliphatic or aromatic, linear or branched, cyclic or acyclic, hydrocarbon, or alpha-olefin, normal alpha-olefin, mono-olefin, diolefin, triolefin, or combinations thereof) may comprises, or consist essentially of, olefins having an even number of carbon atoms; alternatively an odd number of carbon atoms.

In one implementation, the olefin feedstock may comprise, or consist essentially of, olefins having at least 4 carbon atoms; alternatively, at least 6 carbon atoms; alternatively, at least 8 carbon atoms; alternatively, at least 10 carbon atoms; alternatively, at least 12 carbon atoms; alternatively, at least 14 carbon atoms; alternatively, at least 16 carbon atoms; or alternatively, at least 18 carbon atoms. In some implementations, the olefin feedstock may comprise, or consist essentially of, olefins having from 4 to 20 carbon atoms; alternatively, from 6 to 16 carbon atoms; alternatively, from 8 to 14 carbon atoms; alternatively, from 10 to 12 carbon atoms; or mixtures thereof.

In one implementation, the olefin feedstock may comprise, or consist essentially of, alpha-mono-olefins having at least 4 carbon atoms; alternatively, at least 6 carbon atoms; alternatively, at least 8 carbon atoms; alternatively, at least 10 carbon atoms; alternatively, at least 12 carbon atoms; alternatively, at least 14 carbon atoms; alternatively, at least 16 carbon atoms; or alternatively, at least 18 carbon atoms. In some implementations, the olefin feedstock may comprise, or consist essentially of, alpha-mono-olefins having from 4 to 20 carbon atoms; alternatively, from 6 to 16 carbon atoms; alternatively, from 8 to 14 carbon atoms; alternatively, from 10 to 12 carbon atoms; or mixtures thereof. In some implementations, the alpha-mono-olefin is 1-decene.

In one implementation, the olefin feedstock composition comprises an alpha-mono-olefin and at least one of a diolefin having the same number of carbon atoms as the alpha-mono-olefin and/or a triolefin having the same number of carbon atoms as the alpha-mono-olefin. In some implementations, the olefin feedstock composition further comprises at least one of a diolefin having a different number of carbon atoms compared to the alpha-mono-olefin and/or a triolefin having a different number of carbon atoms compared to the alpha-mono-olefin. In some implementations, the olefin feedstock composition further comprises a second alpha-mono-olefin having a different number of carbon atoms compared to the first alpha-mono-olefin.

In one implementation, the olefin feedstock composition comprises 93.5-96% by weight (e.g., 94-96% by weight) of the alpha-mono-olefin, 1-6% by weight of the diolefin, and 0-4% by weight (e.g., 0.5-4% by weight) of the triolefin.

In one implementation, the olefin feedstock composition comprises alpha-mono-olefin and at least one of a diolefin having at least 10 carbon atoms and/or a triolefin having at least 10 carbon atoms. In one implementation, the olefin feedstock composition comprises 93.5-96% by weight (e.g., 94-96% by weight) of 1-decene, 1-6% by weight of the diolefin, and 0-4% by weight (e.g., 0.5-4% by weight) of the triolefin.

Minimally, the feedstock composition comprising the olefin feedstock can comprise any desired olefin feedstock described herein. In one implementation, the feedstock composition comprising the olefin feedstock can further comprise a solvent or diluent. In some implementations, the feedstock composition comprising the olefin feedstock can consist essentially of any olefin feedstock described herein; alternatively consist essentially of any olefin feedstock described herein and any solvent or diluent described herein. Solvents or diluents, which may be utilized in the feedstock composition comprising the olefinic feedstock, are described herein. In other implementations, the feedstock composition comprising the olefin feedstock can be substantially devoid of solvent or diluent.

In one implementation, the olefin feedstock composition is contacted with ethylene in the presence of an olefin metathesis catalyst. The ethylene may be fed into a reactor containing the olefin metathesis catalyst. In some implementations, the ethylene and the olefin feedstock composition flow into the reactor simultaneously. In some implementations, the ethylene and the olefin feedstock composition flow into the reactor sequentially.

Generally, one can use any olefin metathesis catalyst that is capable of producing an alpha-olefin product having the desired purity of alpha-mono-olefin. However, depending upon other metathesis reaction parameters (e.g. olefin feedstock characteristics and/or the metathesis reaction conditions), particular class(es) of olefin metathesis catalyst(s) may be favored in particular instances.

Olefin metathesis catalysts and/or olefin metathesis catalyst systems can be classified by the compound(s) of the olefin metathesis catalyst contacted with the olefin feedstock or the recognized initial olefin metathesis catalyst species. Often the true catalytic species may be difficult to determine because the initial catalytic specie is transformed to other species once the metathesis reaction is initiated. One of ordinary skill in the art will readily recognize the type of olefin metathesis catalyst or olefin metathesis catalyst system based upon the compound(s) contacted with the olefin feedstock. In some instances, one may initially contact a precursor of the olefin metathesis catalyst or olefin metathesis catalyst system to the olefin feedstock and create the olefin metathesis catalyst or olefin metathesis catalyst system in situ. One of skill in the art will readily recognize the particular type of olefin metathesis catalyst and/or olefin metathesis catalyst system from the materials added/contacted with the olefin feedstock. Non-limiting examples of suitable olefin metathesis catalysts include Grubbs catalysts, Hoveyda catalysts, and Schrock catalysts as are known in the art.

Olefin metathesis is a metal-catalyzed redistribution of olefinic (alkenyl) carbon-carbon double bonds between two or more reactants. This work was largely pioneered by Grubbs and Schrock, who shared the 2005 Nobel Prize and who have their names associated with many of the catalyst species utilized for these reactions. See, e.g., R. H. Grubbs, "Olefin Metathesis," Tetrahedron, vol. 60, pp. 7117-7140 (2004); R. R. Schrock et al., "Molybdenum and Tungsten Imido Alkylidene Complexes as Efficient Olefin-Metathesis Catalysts," Angew. Chem. Int. Ed., vol. 42, pp. 4592-4633 (2003); and Trnka et al., "The Development of $L_2X_2Ru=CHR$ Olefin Metathesis Catalysts: An Organometallic Success Story," Acc. Chem. Res., vol. 34, pp. 18-29 (2001).

The olefin metathesis catalyst is a transition metal complex comprising a metal selected from the group consisting of Ni, W, Ru, Mo, Re, and combinations thereof. In one implementation, the olefin metathesis catalyst is a transition metal complex comprising Ru.

In one implementation, the olefin metathesis catalyst can be a metal oxide based olefin metathesis catalyst system, a metal halide based olefin metathesis catalyst system, or a metal carbene based olefin metathesis catalyst system. In some implementations, the olefin metathesis catalyst can be a metal oxide based olefin metathesis catalyst system or a metal halide based olefin metathesis catalyst system. In other implementations, the olefin metathesis catalyst may be a metal oxide based olefin metathesis catalyst system; alternatively, a metal halide based olefin metathesis catalyst system; or alternatively, a metal carbene based olefin metathesis catalyst system.

Examples of suitable metal oxide based olefin metathesis catalysts or catalyst systems (hereafter referred to as "metal oxide olefin metathesis catalyst(s)") can comprise cobalt oxide, molybdenum oxide, tungsten oxide, rhenium oxide, or combinations thereof. In some implementations, the metal oxide olefin metathesis catalyst further comprises a support; alternatively, the metal oxide olefin metathesis catalyst may be unsupported. Suitable metal oxide olefin metathesis catalyst supports include alumina, silica, silica-alumina, and aluminum-phosphate. In further implementations, the metal oxide olefin metathesis catalyst further comprises a metal alkyl activator. Suitable metal alkyl activators for the metal oxide olefin metathesis catalyst are described herein. Non-limiting examples of suitable metal oxide olefin metathesis catalysts include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), and rhenium oxide on alumina activated with tetramethyltin ($Re_2O_7/Al_2O_3/SnMe_4$). Other suitable metal oxide metathesis catalysts are known to those skilled in the art.

Suitable metal halide based olefin metathesis catalysts and/or catalyst systems (hereafter referred to as "metal halide metathesis catalyst(s)") can comprise a halide of tungsten, molybdenum, or a mixture thereof. In one implementation, the halide of the metal halide olefin metathesis catalyst can be chloride, bromide, or iodide; alternatively, chloride; alternatively, bromide; or alternatively, iodide. In some implementations, the metal halide olefin metathesis catalyst can comprise tungsten chloride, molybdenum chloride, or mixtures thereof. In other implementations, the metal halide olefin metathesis catalyst comprises tungsten chloride; or alternatively, molybdenum chloride. Typically, the metal halide olefin metathesis catalyst further comprises a metal alkyl activator. Suitable metal alkyl activators for the metal halide olefin metathesis catalyst are described herein. The metal halide olefin metathesis catalyst can further comprise other agents in addition to the metal halide and metal alkyl activator, for example alcohol or oxygen, to provide and/or increase metathesis activity. Non-limiting examples of metal halide olefin metathesis catalysts include tungsten chloride/tetrabutyltin ($WCl_6/SnMe_4$), tungsten chloride/ethylaluminum dichloride ($WCl_6/EtAlCl_2$), tungsten chloride/ethyl-aluminum dichloride/ethyl alcohol ($WCl_6/EtAlCl_2/EtOH$), molybdenum chloride/triethylaluminum ($MoCl_5/AlEt_3$), and molybdenum chloride/triethylaluminum/$O_2$ ($MoCl_5/AlEt_3/O_2$). Other suitable metal halide metathesis catalysts are known to those skilled in the art.

Typically, the metal alkyl activator for the metal oxide metathesis catalysts or the metal halide metathesis catalysts can comprise, or consist essentially of, any metal alkyl. Suitable metal alkyl compounds can include alkyl lithium, alkyl magnesium, alkyl aluminum, alkyl tin compounds, and mixtures thereof. In some implementations, the metal alkyl compound can be an alkyl lithium compound; alternatively an alkyl magnesium compound; alternatively, an alkyl aluminum compound, or alternatively, an alkyl tin compound. Suitable alkyl aluminum compounds can include trialkylaluminum compounds and/or alkyl aluminum halide compounds. Suitable alkyl groups for the metal alkyl include any $C_1$ to $C_{10}$ hydrocarbyl group; or alternatively, $C_1$ to $C_5$ hydrocarbyl group. In some implementations, the alkyl group for the metal alkyl can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Examples of suitable trialkylaluminum compounds include trimethylaluminum, triethylaluminum, and tributylaluminum. The halide of the alkyl aluminum halide compounds can be can be chloride, bromide, or iodide; alternatively, chloride; alternatively, bromide; or alternatively, iodide. Examples of suitable alkyl aluminum halides include ethyl aluminum dichloride, diethylaluminum chloride, and ethylaluminum sesquichloride. Suitable alkyl tin compounds include tetramethyltin, tetraethyltin, and tetrabutyltin.

Metal carbene olefin metathesis catalysts and/or catalyst systems (hereafter referred to as "metal carbene olefin metathesis catalyst(s)") are characterized by the presence of a metal-carbon double bond. As opposed to the metal oxide and the metal halide olefin metathesis catalysts, the metal carbene olefin metathesis catalysts are compounds, which have a stable metal-carbon double bond or can form a metal-carbon double bond in situ from a metal precursor having a stable metal-carbon single bond.

The metal of suitable metal carbene olefin metathesis catalysts can comprise, or consist essentially of, tungsten, tantalum, osmium, molybdenum, or ruthenium. In one implementation, the metal carbene olefin metathesis catalyst can be a tungsten carbene olefin metathesis catalyst, a molybdenum carbene olefin metathesis catalyst, or a ruthenium carbene olefin metathesis catalyst; or alternatively, a ruthenium carbene olefin metathesis catalysts or molybdenum carbene olefin metathesis catalyst. In some implementations, the metal carbene olefin metathesis catalyst can be a tungsten carbene olefin metathesis catalyst; alternatively, an osmium carbene olefin metathesis catalyst; alternatively, a ruthenium carbene olefin metathesis catalyst; or alternatively, a molybdenum carbene olefin metathesis catalyst.

In one implementation, the ruthenium carbene metathesis catalyst can have the structure $L_1L_2X_2Ru=CHR$ wherein $L_1$ and $L_2$ can be an organic ligand, X is a halide, and R represents hydrogen or a hydrocarbyl group. Further implementations of the groups $L_1$, $L_2$, X, and R, are independently described herein. Generally, the ruthenium carbene metathesis catalyst having the structure $L_1L_2X_2Ru=CHR$ can be described using any combination of $L_1$ described herein, $L_2$ described herein, X described herein, and R described herein.

In one implementation, $L_1$ and $L_2$ of the ruthenium carbene metathesis catalyst having the structure $L_1L_2X_2Ru=CHR$ can independently be $R'_3P$, an imidazolinylidene group, or an imidazolidinylidene group. In some implementations, $L_1$ and $L_2$ are $R'_3P$; alternatively, $L_1$ is $R'_3P$ and $L_2$ is an imidazolinylidene group, or an imidazolidinylidene group; alternatively, $L_1$ is $R'_3P$ and $L_2$ is an imidazolinylidene group; alternatively, $L_1$ is $R'_3P$ and $L_2$ is an imidazolidinylidene group; alternatively, $L_1$ and $L_2$ are imidazolinylidene groups; or alternatively, $L_1$ and $L_2$ are imidazolidinylidene groups.

In one implementation, R' of $R'_3P$ can be a hydrocarbyl group. In some implementations, each R' of $R'_3P$ can be the same; alternatively, each R' of $R'_3P$ can be different; or alternatively, one R' of $R'_3P$ can be different from the other two R's. In some implementations, each R' of $R'_3P$ can be a $C_1$ to $C_{15}$ hydrocarbyl group; or alternatively, a $C_1$ to $C_{10}$ hydrocarbyl group. In other implementations, each hydrocarbyl R' of $R'_3P$ can independently be an alkyl group or an aromatic group; alternatively, an alkyl group; or alternatively, an aromatic group. In one implementation each alkyl R' of $R'_3P$ can independently be a methyl group, ethyl group, n-propyl group, isopropyl group, tert-butyl group, neopentyl group, cyclopentyl group, or cyclohexyl group. In some implementations, one or more R's of $R'_3P$ can be a phenyl group; or alternatively a substituted phenyl group. In one implementation, the substituents of the substituted phenyl group(s) within $R'_3P$ can be a $C_1$-$C_5$ organyl group(s); or alternatively, $C_1$-$C_5$ hydrocarbyl group(s). In some implementations, $R'_3P$ can be a trialkyl phosphine or triphenyl phosphine; alternatively, trialkyl phosphine; or alternatively, triphenyl phosphine. In one implementation, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In one implementation, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; alternatively, a $C_5$ to $C_{40}$ imidazolinylidene group or imidazolidinylidene group. In some implementations, the imidazolinylidene group may be a 1,3-disubstituted imidazolinylidene group. In some implementations, the imidazolidinylidene group may be a 1,3-disubstituted imidazolidinylidene group. In one implementation, each 1,3-substituent of the 1,3-disubstituted imidazolinylidene group or 1,3-disubstituted imidazolidinylidene group can be a hydrocarbyl group. In one implementation, the 1,3-substituents of the 1,3-disubstituted imidazolinylidene group or 1,3-disubstituted imidazolidinylidene group can be a $C_1$ to $C_{30}$ hydrocarbyl group. In some implementations, each 1,3-substituent of the 1,3-disubstituted imidazolinylidene group or 1,3-disubstituted imidazolidinylidene group can independently be a $C_6$ to $C_{20}$ aromatic group or a $C_1$ to $C_{10}$ alkyl groups. In other implementations, the 1,3-substituents of the 1,3-disubstituted imidazolinylidene group or 1,3-disubstituted imidazolidinylidene group can be $C_6$ to $C_{20}$ aromatic groups; or alternatively, $C_1$ to $C_{10}$ alkyl groups. In one implementation, the aromatic group(s) of the 1,3-disubstituted imidazolinylidene group or 1,3-disubstituted imidazolidinylidene group can be a substituted aromatic group. In some implementations, the substituted aromatic group of the 1,3-disubstituted imidazolinylidene group or 1,3-disubstituted imidazolidinylidene group can be a 2-disubstituted phenyl group, a 2,6-disubstituted phenyl group, or, a 2,4,6-trisubstituted phenyl group; alternatively, a 2,6-disubstituted phenyl group; or alternatively, a 2,4,6-trisubstituted phenyl group. Suitable substituents for the substituted phenyl group(s) within the 1,3-disubstituted imidazolinylidene group or 1,3-disubstituted imidazolidinylidene group include any C1 to C10 hydrocarbyl group; or alternatively, any $C_1$ to $C_5$ hydrocarbyl group. In some implementations, each hydrocarbyl group(s) of the substituted phenyl group(s) within the 1,3-disubstituted imidazolinylidene group or 1,3-disubstituted imidazolidinylidene group can independently be a methyl group, ethyl group, n-propyl group, iso-propyl group, n-butyl group, sec-butyl group, or tert-butyl group; alliteratively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some implementations, the 1,3-substituents of the 1,3-disubstituted imidazolinylidene group or 1,3-disubstituted imidazolidinylidene group can be a 2,6-diisopropylphenyl group or a 2,4,6-trimethylphenyl group; alternatively, a 2,6-diisopropylphenyl group; or alternatively, a 2,4,6-trimethylphenyl group.

In one implementation, each X of the ruthenium carbene metathesis catalyst having the structure $L_1L_2X_2Ru=CHR$ can independently be chloride, bromide, or iodide. In some implementations, X can be chloride; alternatively, bromide; or alternatively iodide.

In one implementation, R of the ruthenium carbene metathesis catalyst having the structure $L_1L_2X_2Ru=CHR$ can be hydrogen or a $C_1$ to $C_{20}$ hydrocarbyl group; or alternatively, a $C_1$ to $C_{20}$ hydrocarbyl group. In some implementations, hydrocarbyl group R can be a methyl group (—$CH_3$), an ethyl group (—$CH_2CH_3$), an isopropyl group (—$CH(CH_3)_2$), a tert-butyl group (—$C(CH_3)_3$), a phenyl group (—$C_6H_5$), a 2-methyl-2-propene group (—CH=C($CH_3$)$_2$), or a 2,2-diphenylethene group (—CH=C($C_6H_5$)$_2$). In other implementations, R can be a tert-butyl group (—$C(CH_3)_3$), a phenyl group (—$C_6H_5$), a 2-methyl-2-propene group (—CH=C($CH_3$)$_2$), or a 2,2-diphenylethene group (—CH=C($C_6H_5$)$_2$); alternatively, hydrogen; alternatively, a tert-butyl group (—$C(CH_3)_3$); alternatively, a phenyl group (—$C_6H_5$); alternatively, a tert-butyl group (—$C(CH_3)_3$); alternatively, a phenyl group (—$C_6H_5$); alternatively, a 2-methyl-2-propene group (—CH=C($CH_3$)$_2$); or alternatively, a 2,2-diphenylethene group (—CH=C($C_6H_5$)$_2$).

In some non-limiting implementations, the ruthenium carbene metathesis catalyst can be dichloro(phenylmethylene)bis(tricyclohexyl phosphine)ruthenium, dichloro(3-methyl-2-butenylidene) bis(tricyclohexyl phosphine)ruthenium, dichloro(3-methyl-2-butenylidene)bis(tricyclopentyl phosphine) ruthenium, 1,3-bis-(2,4,6-trimethylphenyl)-2-(imidazolidinyl-idene)(phenylmethylene)-dichloro(tricyclohexyl phosphine)ruthenium, or 1,3-bis-(2,6-diiso-propylphenyl)-2-(imidazolidinylidene)(phenylmethylene)-dichloro(tricyclohexyl phosphine)ruthenium. In some implementations, the ruthenium metal carbene metathesis catalyst can be di-chloro(phenylmethylene)bis(tricyclohexyl phosphine)ruthenium; alternatively, dichloro(3-methyl-2-butenylidene)bis(tricyclohexyl phosphine)ruthenium; alternatively, 1,3-bis-(2,4,6-trimethylphenyl)-2-(imidazolidinylidene)(phenylmethylene)-dichloro(tricyclohexyl phosphine)ruthenium; or alternatively, 1,3-bis-(2,6-diisopropylphenyl)-2-(imidazolidinyl-idene)(phenylmethylene)-dichloro(tricyclohexyl phosphine)ruthenium.

In one implementation, the molybdenum carbene metathesis catalyst can have the structure $Mo(=CHR)(NAr)(OR')_2$ wherein R is a hydrogen or hydrocarbyl group, Ar is a substituted aromatic ring, and R' is a hydrocarbyl group or a halogenated hydrocarbyl group. Further implementations of the groups R, Ar and R' are independently described herein. Generally, the molybdenum carbene metathesis catalyst having the structure $Mo(=CHR)(NAr)(OR')_2$ can be described using any combination of R described herein, Ar described herein, and R' described herein.

In some implementations, R of the molybdenum carbene metathesis catalyst having the structure $Mo(=CHR)(NAr)(OR')_2$ can be hydrogen or a $C_1$ to $C_{20}$ hydrocarbyl group; or alternatively, a $C_1$ to $C_{20}$ hydrocarbyl group. In some implementations, the hydrocarbyl group R can be a methyl group (—$CH_3$), an ethyl group (—$CH_2CH_3$), an isopropyl group (—$CH(CH_3)_2$), a tert-butyl group (—$C(CH_3)_3$), a phenyl group (—$C_6H_5$), a 2-methyl-2-propene group (—CH=C($CH_3$)$_2$), or a 2,2-diphenylethene group (—CH=C($C_6H_5$)$_2$). In other implementations R can be a tert-butyl group (—$C(CH_3)_3$), a phenyl group (—$C_6H_5$), a 2-methyl-2-propene group (—CH=C($CH_3$)$_2$), or a 2,2-diphenylethene group (—CH=C($C_6H_5$)$_2$); alternatively, a tert-butyl group (—$C(CH_3)_3$) or a phenyl group (—$C_6H_5$); alternatively, hydrogen; alternatively, a tert-butyl group (—$C(CH_3)_3$); alternatively, a phenyl group (—$C_6H_5$); alternatively, a 2-methyl-2-propene group (—CH=C($CH_3$)$_2$); or alternatively, a 2,2-diphenylethene group (—H=C($C_6H_5$)$_2$).

In one implementation, the substituted aromatic ring, Ar, of the molybdenum carbene metathesis catalyst having the structure $Mo(=CHR)(NAr)(OR')_2$ can be a $C_6$ to $C_{30}$ aromatic group; alternatively, a $C_6$ to $C_{20}$ aromatic group. In some implementations, the substituted aromatic ring, Ar, is a $C_6$ to $C_{20}$ hydrocarbyl group. In one implementation, each substituent of the substituted aromatic ring, Ar, of the molybdenum carbene metathesis catalyst having the structure $Mo(=CHR)(NAr)(OR')_2$ can independently be a $C_1$ to $C_{10}$ hydrocarbyl group; or alternatively, a $C_1$ to $C_5$ hydrocarbyl group. In some implementations, the substituted aromatic ring, Ar, of the molybdenum carbene metathesis catalyst having the structure $Mo(=CHR)(NAr)(OR')_2$ can be a 2-substituted phenyl group, a 2,6-disubstituted phenyl group, or alternatively, a 2,4,6-trisubstituted phenyl group. In one implementation, each substituent of the substituted aromatic ring can independently be a methyl group (—$CH_3$), an ethyl group (—$CH_2CH_3$), an isopropyl group (—$CH(CH_3)_2$), a tert-butyl group (—$C(CH_3)_3$), or a neopentyl group (—$CH_2C(CH_3)_3$); alternatively; a methyl group (—$CH_3$), an isopropyl group (—$CH(CH_3)_2$), or a tert-butyl group (—$C(CH_3)_3$); alternatively a methyl group (—$CH_3$) or an isopropyl group (—$CH(CH_3)_2$). In some implementations, each substituent of the substituted aromatic ring can independently be a methyl group (—$CH_3$); alternatively, an isopropyl group (—$CH(CH_3)_2$); or alternatively, a tert-butyl group (—$C(CH_3)_3$). In some non-limiting implementations, the substituted aromatic ring, Ar, of the molybdenum carbene metathesis catalyst having the structure $Mo(=CHR)(NAr)(OR')_2$ can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In one implementation, each R' of the molybdenum carbene metathesis catalyst having the structure $Mo(=CHR)(NAr)(OR')_2$ can independently be a $C_1$ to $C_{10}$ organic group; or alternatively a $C_1$ to $C_5$ organic group. In some implementations, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In one implementation, the halogen atoms of the hydrocarbylhalyl group can be fluorine, chlorine, bromine, iodine or combinations thereof; alternatively fluorine; alternatively, chlorine; alternatively, bromine; or alternatively, iodine. In some implementations, each R' of the molybdenum carbene metathesis catalyst having the structure $Mo(=CHR)(NAr)(OR')_2$ can independently be tert-butyl group (—$C(CH_3)_3$), or a hexafluoro-tert-butyl group (—$C(CF_3)_2(CH_3)$)group. In other implementations, $(OR')_2$ can represent a single organic group wherein the two R' groups attached to the oxygen atoms are connected via a bond between any divalent, trivalent, or tetravalent atom with in the R' groups. In further implementations, $(OR')_2$ can represent a single organic group wherein the two R' groups attached to the oxygen atoms are connected via a carbon-carbon bond between any carbon atom of the two R' groups.

In one implementation, the molybdenum carbene metathesis catalyst can be $Mo(=CH-C(CH_3)_3)(N-2,6-diisopropylphenyl)(OC(CH_3)_3)$, $Mo(=CH-C(CH_3)_2(C_6H_5))(N-2,6-diisopropylphenyl)(OC(CH_3)_3)$, $Mo(=CH-C(CH_3)_3)(N-2,6-diisopropylphenyl)-(OC(CH_3)(CF_3)_2)$, or $Mo(=CH-C(CH_3)_2(C_6H_5))(N-2,6-diisopropylphenyl)-(O-C(CH_3)(CF_3))$. In other implementations, the molybdenum metathesis catalyst can be $Mo(=CH-C(CH_3)_3)(N-2,6-diisopropylphenyl)-(OC(CH_3)_3)$; alternatively, $Mo(=CH-C(CH_3)_2(C_6H_5))(N-2,6-diisopropylphenyl)-(OC(CH_3)_3)$; alternatively, $Mo(=CH-C(CH_3)_3)(N-2,6-diisopropylphenyl)-(OC(CH_3)(CF_3)_2)$; or alternatively, $Mo(=CH-C(CH_3)_2(C_6H_5))(N-2,6-diisopropylphenyl)-(OC(CH_3)(CF_3)_2)$.

In some implementations, the metal carbene metathesis catalyst can be tethered to a support. The metal carbene metathesis catalyst can be tethered to the support via any of the ligands, which do not contain the metal-carbon double bond. In one implementation, the metal carbene catalyst support may be a polymer.

Minimally, the catalyst composition comprises the metathesis catalyst (and/or the metathesis catalyst system components). In one implementation, the catalyst composition may consist essentially of the metathesis catalyst (or the metathesis catalyst system components). In one implementation, the catalyst composition comprising the metathesis catalyst can further comprise a solvent or diluent. In some implementations, the catalyst composition comprising the metathesis catalyst consist essentially of the metathesis catalyst (or the metathesis catalyst system components); or alternatively, consist essentially of the metathesis catalyst (or the metathesis catalyst system components) and a solvent or diluent. Solvents or diluents, which may be utilized in the catalyst composition comprising the metathesis catalyst, are described herein. In other implementations, the catalyst composition comprising the metathesis catalyst (or the metathesis catalyst system components) is substantially devoid of solvent or diluent.

The metathesis process can be conducted under any conditions adequate to produce the desired alpha-olefin product having the desired purity of alpha-mono-olefin. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In some implementations, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one implementation, the solvent comprises toluene.

The metathesis reaction temperature may be a rate-controlling variable where the temperature is selected to provide the desired alpha-olefin product having the desired purity of 1-olefin at an acceptable rate. In some implementations, the metathesis reaction temperature is greater than about −40 degrees Celsius, greater than about −20 degrees Celsius, greater than about 0 degrees Celsius, or greater than about 10 degrees Celsius. In some implementations, the metathesis reaction temperature is less than about 150 degrees Celsius, or less than about 120 degrees Celsius. In one implementation, the metathesis reaction temperature is between about 10 degrees Celsius and about 120 degrees Celsius. In one implementation, the metathesis reaction temperature ranges from the melting point of the olefin feedstock composition to 120 degrees Celsius.

The metathesis reaction can be run under any desired pressure. Typically, it will be desirable to maintain a total pressure, which maintains the metathesis reaction solution in a processable state. The total pressure may be selected to be greater than about 0.1 atm (10 kPa), in some implementations greater than about 0.3 atm (30 kPa), or greater than about 1 atm (100 kPa). Typically, the reaction pressure is no more than about 70 atm (7000 kPa), in some implementations no more than about 30 atm (3000 kPa). A non-limiting example of a pressure range for the metathesis reaction is from about 1 atm (100 kPa) to about 30 atm (3000 kPa).

Generally, the metathesis reaction may be carried out for a duration, which can provide an alpha-olefin product having the desired purity of alpha-mono-olefin. The metathesis reaction duration may be dependent upon the identity of the metathesis catalyst used, the molar ratio of metathesis catalyst moieties to moles of olefin feedstock, and the metathesis reaction temperature, among other metathesis reaction parameters (e.g. the identity of the olefin feedstock). In one implementation, the duration of the metathesis reaction can range from 1 minute to 48 hours. In some implementations, the duration of the metathesis reaction can range from 10 minutes to 30 hours. In other implementations, the duration of the metathesis reaction can range from 15 minutes to 24 hours; alternatively, 15 minutes to 12 hours; alternatively, 15 minutes to 6 hours; or alternatively, 15 minutes to 4 hours.

In some implementations, the alpha-olefin product produced by the metathesis reaction conditions has increased alpha-mono-olefin content relative to the alpha-mono-olefin content of the olefin feedstock composition. In some implementations, the alpha-olefin product has an alpha-mono-olefin content of about 95 wt. % or greater; about 96 wt. % or greater; about 97 wt. % or greater; about 98 wt. % or greater; or about 99 wt. % or greater of the total weight of the alpha-olefin product.

In some implementations, the alpha-olefin product includes alpha-mono-olefin, alpha-olefins having less than 10 carbon atoms and branched internal olefins. In some implementations, the alpha-olefins have less than 10 carbon atoms. In some implementations, the alpha-olefins are linear terminal olefins. In some implementations, the alpha-olefins having less than 10 carbon atoms comprise $C_4$-$C_7$ terminal olefins.

In some implementations, the alpha-mono-olefin in the alpha-olefin product is separated from the alpha-olefin product by a distillation process. The distillation process removes the lower boiling fragments from the alpha-olefin product increasing the purity of alpha-mono-olefin present.

In some implementations where it is desirable to achieve higher purity, metathesis and distillation processes may be repeated.

In another implementation, the method comprises (1) providing an olefin feedstock composition comprising an alpha-mono-olefin and vinylidene olefin(s), (2) reacting the olefin feedstock composition in the presence of an isomerization catalyst to form an isomerized olefin feedstock comprising the alpha-mono-olefin and branched internal olefins formed from the vinylidene olefins, (3) providing a catalyst composition having an olefin metathesis catalyst, and (4) reacting the isomerized olefin feedstock composition and ethylene at metathesis reaction conditions in the presence of the olefin metathesis catalyst to produce an alpha-olefin product having the alpha-mono-olefin, linear and branched olefins having fewer carbon atoms than the olefin feedstock.

Figure 2:
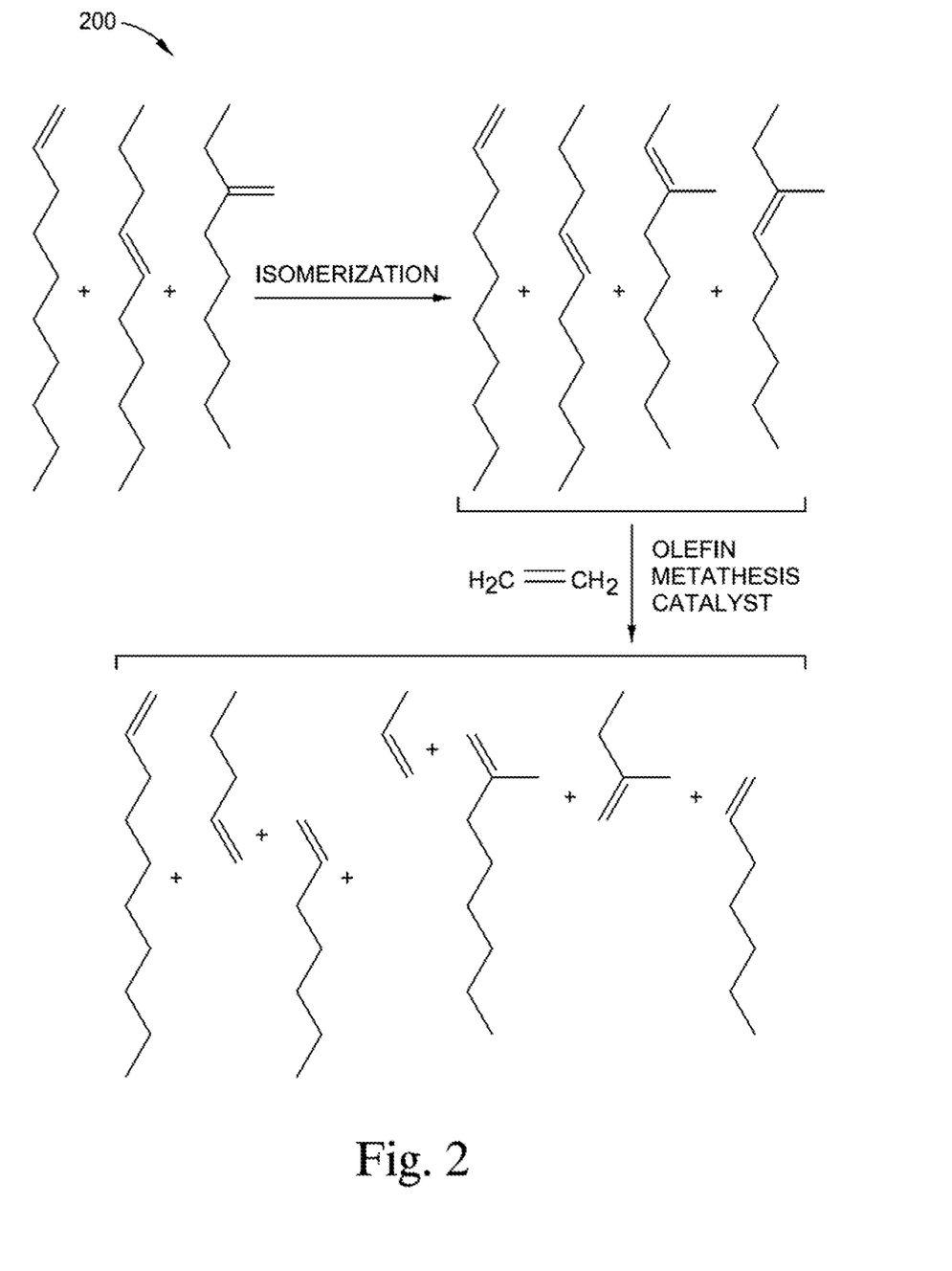
FIG. 2 depicts a second example of a reaction scheme for increasing olefin content according to one or more implementations of the present disclosure.

FIG. 2 depicts a second example of a reaction scheme 200 for increasing olefin content according to one or more implementations of the present disclosure. The second reaction scheme 200 is similar to the first reaction scheme 100, except that the second reaction scheme 200 includes an additional isomerization process, which is performed prior to contacting the isomerized olefin feedstock composition with ethylene in the presence of a catalyst composition comprising an olefin metathesis catalyst. In addition to 1-decene, the alpha-olefin feedstock used in reaction scheme 200 includes a vinylidene olefin. Isomerization is preferably achieved with a catalyst that does not isomerize the desired 1-decene product but easily converts the vinylidene olefins into branched internal olefins. Examples of catalysts that may be used with the implementations described herein are disclosed in U.S. Pat. No. 6,730,750, which is herein incorporated by reference in its entirety. Not to be bound by theory, but it is believed that the alpha-mono-olefin (e.g., 1-decene) goes through the metathesis reaction unchanged while the vinylidene olefins and internal olefins react under the metathesis reaction conditions to form lower molecular weight olefins, which can be easily removed by distillation.

Referring to FIG. 2, in another implementation, the method comprises (1) providing an olefin feedstock composition comprising 1-decene and vinylidene olefins, (2) reacting the olefin feedstock composition in the presence of a zeolite catalyst to form an isomerized olefin feedstock comprising 1-decene and branched internal olefins formed from the vinylidene olefin(s), (3) contacting the isomerized olefin feedstock composition with ethylene in the presence of a catalyst composition comprising an olefin metathesis catalyst, and (4) reacting the isomerized olefin feedstock composition and ethylene at metathesis reaction conditions to produce a product comprising 1-decene, linear and branched olefins having less than 10 carbon atoms.

The olefin feedstock composition may be an olefin feedstock composition as previously described herein. In one implementation, the olefin feedstock composition comprises 1-olefin and vinylidene olefin(s). In one implementation, the olefin feedstock composition comprises 90-97% by weight (e.g., 92-96% by weight; or 92-94% by weight) of 1-olefin and 1-8% of the vinylidene olefin(s) and optionally 0.5-4% of a linear internal olefin. In one implementation, the olefin feedstock composition comprises 90-97% by weight (e.g., 92-96% by weight; or 92-94% by weight) of 1-decene and 1-8% of a vinylidene olefin(s) and optionally 0.5-4% of a linear internal olefin.

In one implementation, the olefin feedstock may comprise, or consist essentially of, vinylidene olefin(s) having at least 4 carbon atoms; alternatively, at least 6 carbon atoms; alternatively, at least 8 carbon atoms; alternatively, at least 10 carbon atoms; alternatively, at least 12 carbon atoms; alternatively, at least 14 carbon atoms; alternatively, at least 16 carbon atoms; alternatively, at least 18 carbon atoms; or mixtures thereof. In some implementations, the olefin feedstock may comprise, or consist essentially of, vinylidene olefin(s) having from 4 to 20 carbon atoms; alternatively, from 6 to 16 carbon atoms; alternatively, from 8 to 14 carbon atoms; or alternatively, from 10 to 12 carbon atoms. In some implementations, the vinylidene olefin(s) include a $C_{10}$ vinylidene olefin.

In one implementation, the olefin feedstock may comprise, or consist essentially of, linear internal olefin(s) having at least 4 carbon atoms; alternatively, at least 6 carbon atoms; alternatively, at least 8 carbon atoms; alternatively, at least 10 carbon atoms; alternatively, at least 12 carbon atoms; alternatively, at least 14 carbon atoms; alternatively, at least 16 carbon atoms; alternatively, at least 18 carbon atoms; or mixtures thereof. In some implementations, the olefin feedstock may comprise, or consist essentially of, linear internal olefin(s) having from 4 to 20 carbon atoms; alternatively, from 6 to 16 carbon atoms; alternatively, from 8 to 14 carbon atoms; or alternatively, from 10 to 12 carbon atoms. In some implementations, the linear internal olefin(s) include a $C_{10}$ linear internal olefin.

In one implementation, the olefin feedstock composition is reacted in the presence of an isomerization catalyst to form an isomerized olefin feedstock comprising an alpha-mono-olefin, branched internal olefins formed from the vinylidene olefin(s), and optionally the linear internal olefin. It is contemplated that any isomerization process, which converts substantially all of the vinylidene olefins into branched internal olefins while leaving the alpha-mono-olefin unreacted, may be utilized in accordance with the present disclosure. Examples of isomerization processes and catalysts that may be used with the implementations described herein are described in U.S. Pat. No. 6,730,750, which is incorporated herein in its entirety.

In one implementation, isomerization of the olefin feedstock composition may be performed by contacting the olefin feedstock composition with a zeolite catalyst. In one implementation, the zeolite catalyst includes LZ-Y52 zeolite under olefin isomerization reaction conditions. The LZ-Y52 zeolite catalyst material commercially available from Union Carbide Corporation. The LZ-Y52 material is a synthetic crystalline aluminosilicate of a cubic arrangement having a density of 1.3 g/cc and having the following formula:

$$Na_{56}[(AlO_2)_{56}(SiO_2)_{136}]264H_2O$$

LZ-Y52 can be made in, and is commercially available in, various shapes. For example, LZ-Y52 is available as ⅛ inch or {fraction (1/16)} inch extrudate pellets.

LZ-Y52 has been described as a Y zeolite, in particular a sodium Y zeolite, which is an excellent starting material if high ion exchange capacity is desired. LZ-Y52 can be converted to LZ-Y62 by cation exchange of ammonium for sodium, with the sodium content of LZ-Y52 reduced by 80%. The chemical and physical properties of LZ-Y52 compared to LZ-Y62 are as follows: $Na_2O$, 13 wt. % vs 2.5 wt. % for LZ-Y62; $(NH_4)_2O$, none vs 9.8 wt. % for LZ-Y62; $Na^+$ to Al molar ratio, 0.934 vs 0.18 for LZ-Y62; $NH^{4+}$ to Al ratio, none vs 0.862 for LZ-Y62; 02 capacity, 33.6 wt. % vs 34.0 for LZ-Y62; and cell dimension "a" of 24.68 for LZ-Y52 vs 24.73 for LZ-Y62.

In some implementations, suitable temperatures for use in the isomerization process are between 10 degrees Celsius and 150 degrees Celsius (e.g., between 30 degrees Celsius and 120 degrees Celsius; or between 35 degrees Celsius and 100 degrees Celsius. In some implementations, suitable pressures for use in the isomerization process of the present disclosure are between 1 and 5000 psia (e.g., between 10 and 100 psia; or between 15 and 45 psia). In one implementation, suitable weight hourly space velocities (WHSV) for use in the isomerization process of the present invention are between 0.1 and 100 (between 1 and 50; or between 2 and 20). The WHSV is computed as the weight of feed per hour to the reactor divided by the weight of catalyst in the reactor.

In some implementations, the isomerized olefin feedstock comprises the alpha-mono-olefin, branched internal olefins formed from the vinylidene olefin(s), and optionally the linear internal olefin. In some implementations, the branched internal olefins have the same number of carbon atoms as the vinylidene olefin(s). In some implementations, the branched internal olefin(s) include $C_{10}$ branched internal olefins. In some implementations, the isomerized olefin feedstock further comprises linear internal olefin(s). In some implementations, the linear internal olefin(s) have the same number of carbon atoms as the alpha-mono-olefin. In some implementations, the linear internal olefin(s) includes $C_{10}$ linear internal olefins as depicted in FIG. 2.

In some implementations, the isomerized olefin feedstock composition is contacted with ethylene in the presence of a catalyst composition comprising an olefin metathesis catalyst. The ethylene may be fed into a reactor containing the olefin metathesis catalyst. In some implementations, the ethylene and the olefin feedstock composition flow into the reactor simultaneously. In some implementations, the ethylene and the olefin feedstock composition flow into the reactor sequentially.

Generally, one can use any olefin metathesis catalyst that is capable of producing an alpha-olefin product having the desired purity of the alpha-mono-olefin. However, depending upon other metathesis reaction parameters (e.g. olefin feedstock characteristics and/or the metathesis reaction conditions), particular class(es) of olefin metathesis catalyst(s) may be favored in particular instances. Suitable olefin metathesis catalysts have been previously described herein.

The isomerized olefin feedstock composition and ethylene are reacted at metathesis reaction conditions to produce the desired alpha-olefin product. Suitable metathesis reaction conditions have also been previously described herein.

In some implementations, the alpha-olefin product includes the alpha-mono-olefin, linear and branched olefins having fewer carbon atoms than the alpha-mono-olefin present in the olefin feedstock composition. In some implementations, the linear olefin(s) have fewer than 10 carbon atoms. In some implementations, the linear olefin(s) include $C_4$-$C_9$ linear olefins. In some implementations, the branched olefin(s) have fewer than 10 carbon atoms. In some implementations, the branched olefin(s) include $C_4$-$C_9$ branched olefins.

In some implementations, the alpha-olefin product includes 1-decene, linear and branched olefins having less than 10 carbon atoms.

In some implementations, the alpha-olefin product includes the alpha-mono-olefin, terminal olefins and branched olefins having fewer carbon atoms than the alpha-mono-olefin. In some implementations, the terminal olefins and branched olefins have less than 10 carbon atoms. In some implementations, the terminal olefins are linear terminal olefins. In some implementations, the terminal olefins include $C_4$-$C_9$ terminal olefins.

In some implementations, the alpha-mono-olefin in the alpha-olefin product is separated from the linear and branched olefins having fewer carbon atoms than the alpha-mono-olefin by a distillation process. The distillation process removes the lower boiling fragments from the alpha-olefin product increasing the purity of the alpha-mono-olefin (e.g., 1-decene) present.

In some implementations, the purified alpha-olefin product has an alpha-mono-olefin content of about 95 wt. % or greater; about 96 wt. % or greater; about 97 wt. % or greater; about 98 wt. % or greater; or about 99 wt. % or greater of the total weight of the alpha-olefin product.

In some implementations where it is desirable to achieve higher purity, the isomerization, metathesis and distillation processes may be repeated.

In some implementations, the alpha-olefin product may be used to form a drag reducing agent. The drag reducing agent may be formed by methods known in the art. In one implementation, the drag reducing agent may be produced by bulk polymerization of the alpha-olefin product in the presence of a catalyst. The bulk polymerization may be carried out using any olefin polymerization catalyst. In one implementation, the bulk polymerization is carried out in the presence of Ziegler-Natta catalysts. In one implementation, the catalyst system includes a transition metal catalyst and a co-catalyst mixture. The catalyst and co-catalysts may be added as additives at any time during the polymerization process. The concentration of catalyst, which is optimum, depends upon the dimensions of the reaction vessel.

In one implementation, the catalyst and the alpha-olefin product are combined in a reaction vessel and agitated at ambient conditions for a period of time sufficient to increase viscosity of the reactants sufficiently to suspend the catalyst and then placed into a cool environment to allow the reaction to proceed. The cool environment is normally maintained at a temperature from about −20 degrees Celsius to about 25 degrees Celsius, allowing the reaction to proceed at a relatively constant pace, while removing heat and forming ultrahigh molecular weight polymers. After bulk polymerization, the material is reduced in size by a method such as cryogenic grinding, and slurried in water, alcohol, or a water-alcohol carrier fluid to obtain a drag reducing agent with the desired viscosity. Additional additives such as surfactants, biocides and defoamers can be added to the drag reducing agent as needed.

Figure 3:
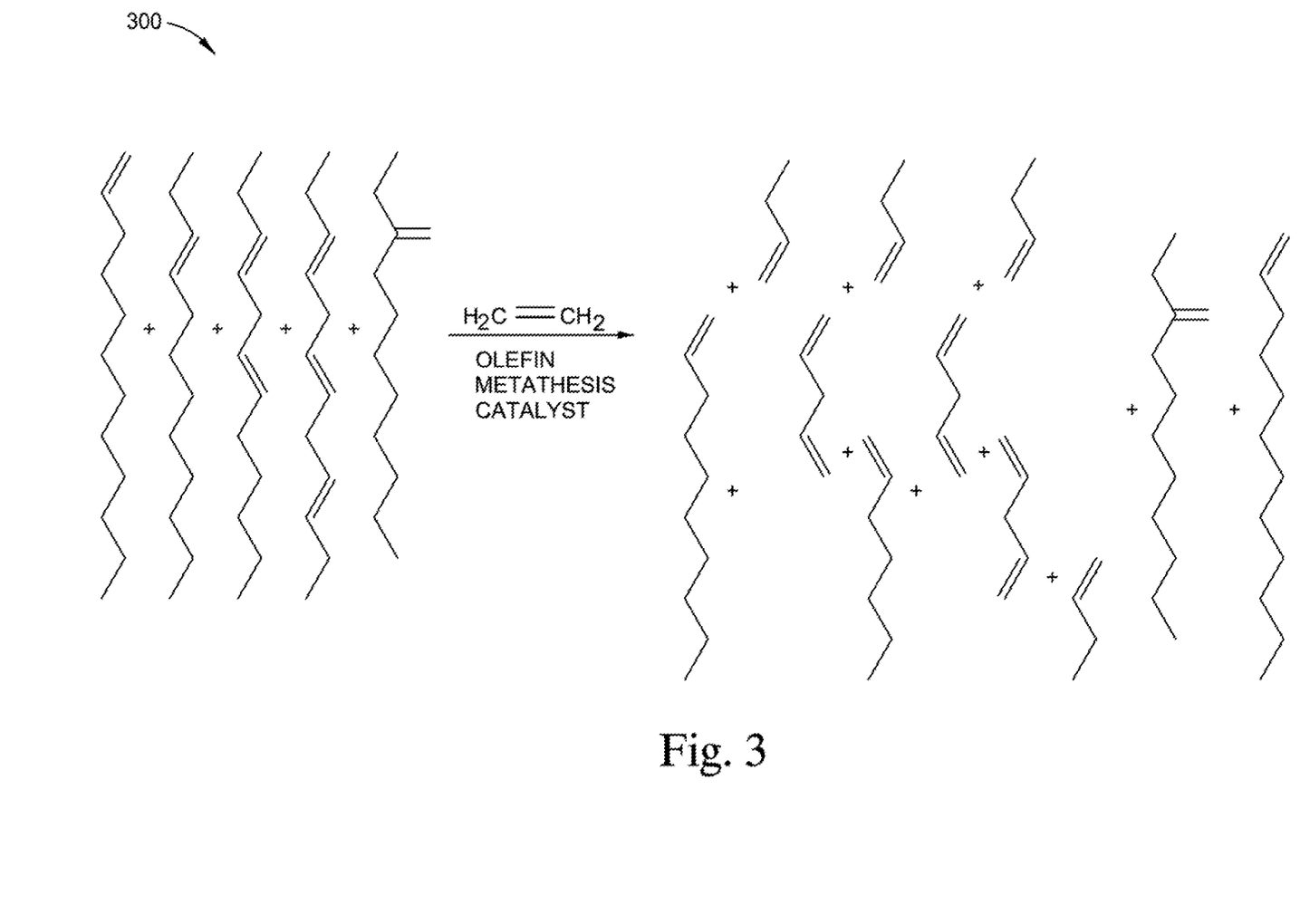
FIG. 3 depicts a third example of a reaction scheme for increasing olefin content according to one or more implementations of the present disclosure.

FIG. 3 depicts a third example of a reaction scheme 300 for increasing olefin content according to one or more implementations of the present disclosure. The third reaction scheme 300 is similar to the first reaction scheme 100, except that the olefin feedstock composition used for reaction scheme 300 differs. Referring to FIG. 3, in another implementation, the method comprises (1) providing an olefin feedstock composition comprising a linear internal mono-olefin (e.g., 3-dodecene) and optionally at least one of an alpha-olefin having more than 10 carbon atoms (e.g., 1-dodecene), a diolefin (e.g., an internal diolefin), a triolefin (e.g., an internal triolefin) and a vinylidene (e.g., 2-ethyl-1-decene). In one implementation, the olefin feedstock composition comprises 3-dodecene and at least one of an alpha-olefin having at least 12 carbon atoms, a diolefin having at least 12 carbon atoms, a triolefin having at least 12 carbon atoms, and/or a vinylidene having at least 12 carbon atoms. The method further includes (2) providing a catalyst composition having an olefin metathesis composition. The method further includes (3) reacting the olefin feedstock composition with ethylene at metathesis reaction conditions in the presence of the catalyst composition to produce a product composition comprising an alpha-mono olefin product (e.g., 1-decene) and one or more alpha-olefins having less than 10 carbon atoms. In some implementations, the product composition further comprises at least one of the alpha-olefin having more than 10 carbon atoms and the vinylidene. Separation by a method such as distillation results in a fraction that is highly enriched in the alpha-mono olefin product (e.g., 1-decene).

In some implementations, a method is provided. The method includes providing an olefin feedstock composition comprising an alpha-mono-olefin and at least one of a diolefin having the same number of carbon atoms as the alpha-mono-olefin and/or a triolefin having the same number of carbon atoms as the alpha-mono-olefin. The method further includes providing a catalyst composition comprising an olefin metathesis catalyst. The method further includes reacting the olefin feedstock composition and ethylene at metathesis reaction conditions in the presence of the catalyst composition to produce an alpha-olefin product comprising the alpha-mono-olefin and one or more alpha-olefins having fewer carbon atoms than the alpha-mono-olefins.

In one or more implementations described herein, the method further includes separating the alpha-mono-olefin in the alpha-olefin product from the alpha-olefin product using a distillation process.

In one or more implementations described herein, the one or more alpha-olefins having fewer carbon atoms than the alpha-mono-olefin comprise $C_4$-$C_7$ alpha-olefins.

In one or more implementations described herein, the one or more alpha-olefins having fewer carbon atoms than the alpha-mono-olefin include at least one of alpha-mono-olefins and diolefins.

In one or more implementations described herein, the olefin feedstock composition comprises 93.5-96% by weight of the alpha-mono-olefin, 1-6% by weight of the diolefin, and 0.5-4% by weight of the triolefin.

In one or more implementations described herein, the olefin metathesis catalyst is a transition metal complex comprising a metal selected from the group consisting of Ni, W, Ru, Mo, Re, and combinations thereof.

In one or more implementations described herein, the olefin metathesis catalyst is a transition metal complex comprising Ru.

In one or more implementations described herein, the olefin metathesis catalyst is a Grubb's catalyst, a Schrock catalyst, or a Hoveyda catalyst.

In one or more implementations described herein, the olefin metathesis catalyst is selected from a ruthenium carbene metathesis catalyst and a molybdenum carbene metathesis catalyst.

In one or more implementations described herein, the olefin metathesis catalyst is dichloro(phenylmethylene) bis(tricyclohexylphosphine) ruthenium or 1,3-bis-(2,4,6-trimethylphenyl)-2-(imidazolidinylidene)(phenylmethylene)-dichloro(tricyclohexylphosphine)ruthenium.

In one or more implementations described herein, the metathesis reaction conditions comprise a metathesis reaction temperature ranging from the melting point of the olefin feedstock to 120 degrees Celsius.

In one or more implementations described herein, the method further includes polymerizing the alpha-olefin product in the presence of a catalyst to form a drag reducing agent.

In one or more implementations described herein, the alpha-mono-olefin has from 4 to 20 carbon atoms.

In one or more implementations described herein, the alpha-mono-olefin has from 6 to 16 carbon atoms.

In one or more implementations described herein, the alpha-mono-olefin has from 8 to 14 carbon atoms.

In one or more implementations described herein, the alpha-mono-olefin has from 10 to 12 carbon atoms.

In one or more implementations described herein, the alpha-mono-olefin has 10 carbon atoms.

In one or more implementations described herein, the olefin feedstock composition further comprises at least one of a diolefin having a different number of carbon atoms compared to the alpha-mono-olefin and/or a triolefin having a different number of carbon atoms compared to the alpha-mono-olefin.

In one or more implementations described herein, the olefin feedstock composition further comprises a second alpha-mono-olefin having a different number of carbon atoms compared to the first alpha-mono-olefin.

In some implementations, a method is provided. The method includes providing an olefin feedstock composition comprising an alpha-mono-olefin and vinylidene olefins. The method further includes reacting the olefin feedstock composition in the presence of an isomerization catalyst to form an isomerized olefin feedstock comprising the alpha-mono-olefin and branched internal olefins formed from the vinylidene olefins. The method further includes reacting the isomerized olefin feedstock composition and ethylene at metathesis reaction conditions in the presence of a catalyst composition comprising an olefin metathesis catalyst to produce an alpha-olefin product comprising the alpha-mono-olefin, linear and branched olefins having fewer carbon atoms than the olefins in the olefin feedstock composition.

In one or more implementations described herein, the olefin feedstock composition further comprises linear internal olefins.

In one or more implementations described herein, the method further includes separating the alpha-mono-olefin in the alpha-olefin product from the linear and branched olefins having fewer carbon atoms using a distillation process.

In one or more implementations described herein, the linear olefins comprise $C_4$-$C_9$ linear olefins.

In one or more implementations described herein, the branched olefins comprise $C_5$-$C_9$ branched olefins.

In one or more implementations described herein, the olefin feedstock composition comprises 90-97% by weight of the alpha-mono-olefin and 1-8% of the vinylidene olefins.

In one or more implementations described herein, the olefin metathesis catalyst is a transition metal complex comprising a metal selected from the group consisting of Ni, W, Ru, Mo, Re, and combinations thereof.

In one or more implementations described herein, the olefin metathesis catalyst is a transition metal complex comprising Ru.

In one or more implementations described herein, the olefin metathesis catalyst is a Grubb's catalyst, a Schrock catalyst, or a Hoveyda catalyst.

In one or more implementations described herein, the olefin metathesis catalyst is selected from a ruthenium carbene metathesis catalyst and a molybdenum carbene metathesis catalyst.

In one or more implementations described herein, the olefin metathesis catalyst is dichloro(phenylmethylene) bis(tricyclohexylphosphine) ruthenium or 1,3-bis-(2,4,6-trimethylphenyl)-2-(imidazolidinylidene)(phenylmethylene)-dichloro(tricyclohexylphosphine)ruthenium.

In one or more implementations described herein, the metathesis reaction conditions comprise a metathesis reaction temperature ranging from the melting point of the olefin feedstock to 120 degrees Celsius.

In one or more implementations described herein, the isomerization catalyst is a zeolite catalyst.

In one or more implementations described herein, the zeolite catalyst is a synthetic crystalline aluminosilicate of a cubic arrangement having a density of 1.3 g/cc and having the following formula: $Na_{56}[(AlO_2)_{56}(SiO_2)_{136}]_{264}H_2O$.

In one or more implementations described herein, the method further includes polymerizing the alpha-olefin product in the presence of a catalyst to form a drag reducing agent.

In one or more implementations described herein, the alpha-mono-olefin has from 4 to 20 carbon atoms.

In one or more implementations described herein, the alpha-mono-olefin has from 6 to 16 carbon atoms.

In one or more implementations described herein, the alpha-mono-olefin has from 8 to 14 carbon atoms.

In one or more implementations described herein, the alpha-mono-olefin has from 10 to 12 carbon atoms.

In one or more implementations described herein, the alpha-mono-olefin has 10 carbon atoms.

In one or more implementations described herein, the olefin feedstock composition further comprises at least one of diolefins and/or triolefins.

While the foregoing is directed to implementations of the present disclosure, other and further implementations of the present disclosure may be devised without departing from the basic scope thereof, and the scope thereof is determined by the claims that follow.

The invention claimed is:

1. A method, comprising:
   providing an olefin feedstock composition comprising a linear internal olefin;
   providing a catalyst composition comprising an olefin metathesis catalyst;
   reacting the olefin feedstock composition and ethylene at metathesis reaction conditions in the presence of the catalyst composition to produce an alpha-olefin product comprising 1-decene and one or more alpha-olefins having fewer carbon atoms than the linear internal olefin;
   separating the one or more alpha-olefins from the alpha-olefin product using a distillation process; and
   polymerizing the separated alpha-olefin product in the presence of a catalyst to form a drag reducing agent.

2. The method of claim 1, wherein the alpha-olefin product further comprises the alpha-mono-olefin having the same number of carbon atoms as the linear internal olefin.

3. The method of claim 1, wherein the one or more alpha-olefins having fewer carbon atoms than the linear internal olefin comprise $C_4$-$C_7$ alpha-olefins.

4. The method of claim 3, wherein the metathesis reaction conditions comprises a metathesis reaction temperature ranging from the melting point of the olefin feedstock to 120 degrees Celsius.

5. The method of claim 1, wherein the one or more alpha-olefins having fewer carbon atoms than the linear internal olefin include at least one of alpha-mono-olefins and diolefins.

6. The method of claim 1, wherein the olefin metathesis catalyst is a transition metal complex comprising a metal selected from the group consisting of Ni, W, Ru, Mo, Re, and combinations thereof.

7. The method of claim 6, wherein the olefin metathesis catalyst is a transition metal complex comprising Ru.

8. The method of claim 1, wherein the olefin metathesis catalyst is a Grubb's catalyst, a Schrock catalyst, or a Hoveyda catalyst.

9. The method of claim 1, wherein the olefin metathesis catalyst is selected from a ruthenium carbene metathesis catalyst and a molybdenum carbene metathesis catalyst.

10. The method of claim 1, wherein the olefin metathesis catalyst is dichloro(phenylmethylene) bis(tricyclohexylphosphine) ruthenium or 1,3-bis-(2,4,6-trimethylphenyl)-2-(imidazolidinylidene)(phenylmethylene)-dichloro(tricyclohexylphosphine)ruthenium.

11. The method of claim 1, wherein the metathesis reaction conditions comprises a metathesis reaction temperature ranging from the melting point of the olefin feedstock to 120 degrees Celsius.

12. The method of claim 1, wherein the alpha-mono-olefin has from 4 to 20 carbon atoms.

13. The method of claim 1, wherein the olefin feedstock composition further comprises at least one of an alpha-mono-olefin having the same number of carbon atoms as the linear internal olefin, a vinylidene, a diolefin having the same number of carbon atoms as the linear internal olefin, and/or a triolefin having the same number of carbon atoms as the linear internal olefin.

14. A method, comprising:
   providing an olefin feedstock composition comprising 3-dodecene and optionally at least one of an alpha-olefin having at least 12 carbon atoms, a vinylidene having at least 12 carbon atoms, a diolefin having at least 12 carbon atoms, and/or a triolefin having at least 12 carbon atoms;
   providing a catalyst composition comprising an olefin metathesis catalyst; and
   reacting the olefin feedstock composition and ethylene at metathesis reaction conditions in the presence of the catalyst composition to produce an alpha-olefin product comprising 1-decene, and one or more alpha-olefins having fewer carbon atoms than 1-decene.

15. The method of claim 14, further comprising separating the one or more alpha-olefins from the alpha-olefin product using a distillation process.

16. The method of claim 14, wherein the one or more alpha-olefins having fewer carbon atoms than 1-decene comprise $C_4$-$C_7$ alpha-olefins.

17. The method of claim 14, wherein the one or more alpha-olefins having fewer carbon atoms than the 1-decene comprise at least one of alpha-mono-olefins and diolefins.

18. The method of claim 14, wherein the olefin metathesis catalyst is a transition metal complex comprising a metal selected from the group consisting of Ni, W, Ru, Mo, Re, and combinations thereof.

19. The method of claim 14, wherein the olefin metathesis catalyst is a Grubb's catalyst, a Schrock catalyst, or a Hoveyda catalyst.

20. The method of claim 14, wherein the olefin metathesis catalyst is selected from a ruthenium carbene metathesis catalyst and a molybdenum carbene metathesis catalyst.

21. The method of claim 14, further comprising polymerizing the alpha-olefin product in the presence of a catalyst to form a drag reducing agent.

22. A method comprising:
   providing an olefin feedstock composition comprising a linear internal-mono-olefin and at least one of an alpha-olefin having more than 10 carbon atoms, a vinylidene olefin, a diolefin, a triolefin, and combinations thereof;
   providing a catalyst composition comprising an olefin metathesis catalyst; and reacting the olefin feedstock composition and ethylene at metathesis reaction conditions in the presence of the catalyst composition to produce an alpha-olefin product comprising an alpha-mono-olefin and one or more alpha-olefins having fewer carbon atoms than the alpha mono-olefin.

23. The method of claim 22, further comprising separating the alpha-mono-olefin in the alpha-olefin product from the one or more alpha-olefins having fewer carbon atoms than the alpha mono-olefin using a distillation process.

24. The method of claim 22, wherein the one or more alpha-olefins having fewer carbon atoms than the alpha-mono-olefin comprise $C_4$-$C_7$ alpha-olefins.

25. The method of claim 22, wherein the one or more alpha-olefins having fewer carbon atoms than the alpha-mono-olefin include at least one of alpha-mono-olefins and diolefins.

26. The method of claim 22, wherein the alpha-mono-olefin is 1-decene.

27. The method of claim 22, wherein the alpha-mono-olefin having more than 10 carbon atoms has 12 carbon atoms.

28. A method, comprising:
providing an olefin feedstock composition comprising a linear internal olefin and optionally at least one of an alpha-mono-olefin having the same number of carbon atoms as the linear internal olefin, a vinylidene, a diolefin having the same number of carbon atoms as the linear internal olefin, and/or a triolefin having the same number of carbon atoms as the linear internal olefin;
providing a catalyst composition comprising an olefin metathesis catalyst;
reacting the olefin feedstock composition and ethylene at metathesis reaction conditions in the presence of the catalyst composition to produce an alpha-olefin product comprising 1-decene and one or more $C_4$-$C_7$ alpha-olefins; and
separating the one or more $C_4$-$C_7$ alpha-olefins from the alpha-olefin product using a distillation process.

* * * * *